United States Patent [19]
Saito et al.

[11] Patent Number: 5,831,127
[45] Date of Patent: Nov. 3, 1998

[54] BISAMINOTHIOPHENOL COMPOUND

[75] Inventors: Satoru Saito; Haruyoshi Tatsu, both of Ibaraki, Japan; Lev Solomonovich German, deceased, late of Moscow, Russian Federation, by Elena N. German, legal representative; Valerii Romanovich Polishchuk, deceased, late of Lod, Israel, by Margarita Polishchuk, legal representative

[73] Assignee: Nippon Mektron Limited, Tokyo, Japan

[21] Appl. No.: 547,030

[22] Filed: Oct. 23, 1995

[30] Foreign Application Priority Data

Oct. 21, 1995 [JP] Japan ..................... 6-282942

[51] Int. Cl.$^6$ .................................................. C07C 323/35
[52] U.S. Cl. ........................................... 564/335; 564/430
[58] Field of Search ....................... 564/335, 430

[56] References Cited

U.S. PATENT DOCUMENTS 4,864,008  9/1989  Murata et al. .......................... 528/125

*Primary Examiner*—Richard L. Raymond
*Attorney, Agent, or Firm*—Barnes & Thornburg

[57] ABSTRACT

A novel bisaminothiophenol compound represented by the following general formula:

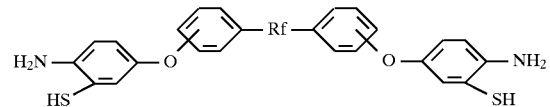

where Rf is a perfluoroalkylidene group having 1 to 10 carbon atoms, is used as a cross-linking agent for fluorine-containing elastomers having CN groups as cross-linkable groups.

6 Claims, No Drawings

BISAMINOTHIOPHENOL COMPOUND

BACKGROUND OF THE INVENTION

1. Field of the Invention

The present invention relates to a bisaminothiophenol compound or its salt, and more particularly to a bisaminothiophenol compound or its salt effectively applicable as a cross-linking agent for fluorine-containing elastomers having CN groups as cross-linkable groups.

2. Related Prior Art

The following bisaminothiophenol compounds are known and are used as raw materials for polybenzothiazoles as heat-resistant resins.

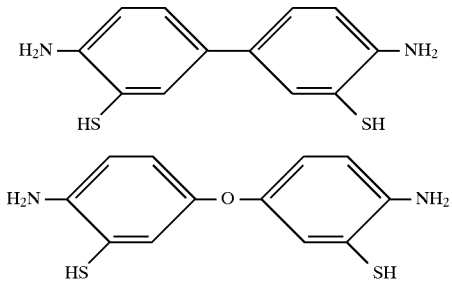

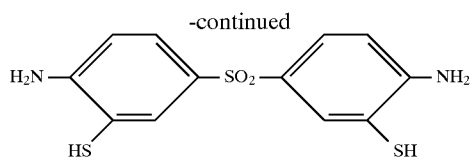

SUMMARY OF THE INVENTION

An object of the present invention is to provide a novel bisaminothiophenol compound represented by the following general formula:

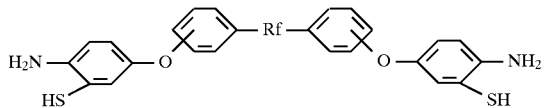

where Rf is a perfluoroalkylidene group having 1 to 10 carbon atoms, which can form salts, such as hydrochloride, hydrobromide, sulfate, borate, carboxylate, etc.

DETAILED DESCRIPTION OF THE INVENTION

The present bisaminothiophenol compound can be produced according to a known synthesis process comprising a series of the following steps:

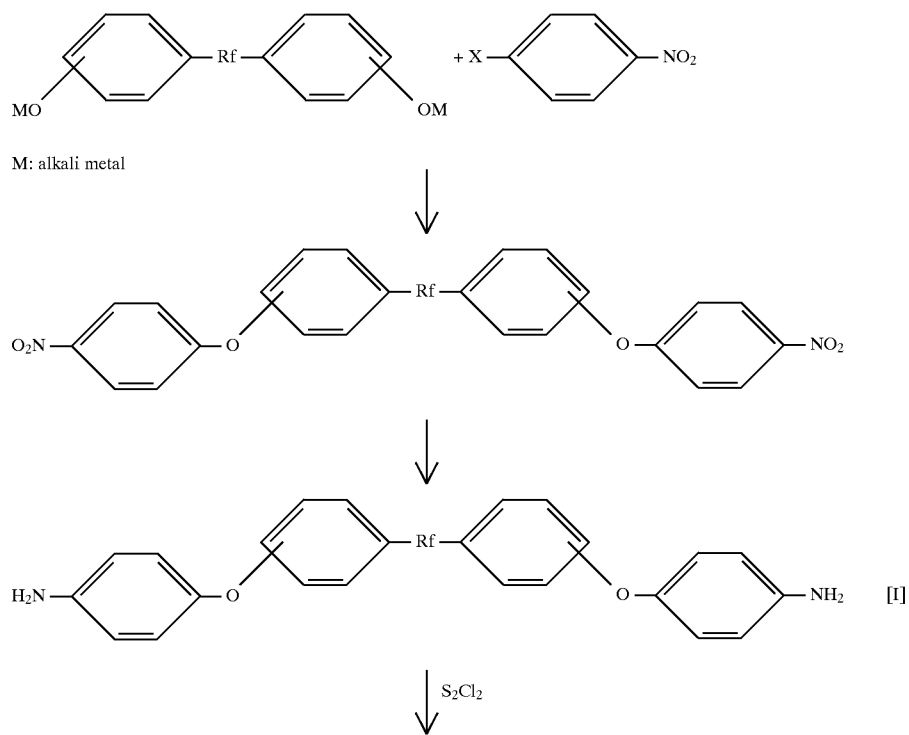

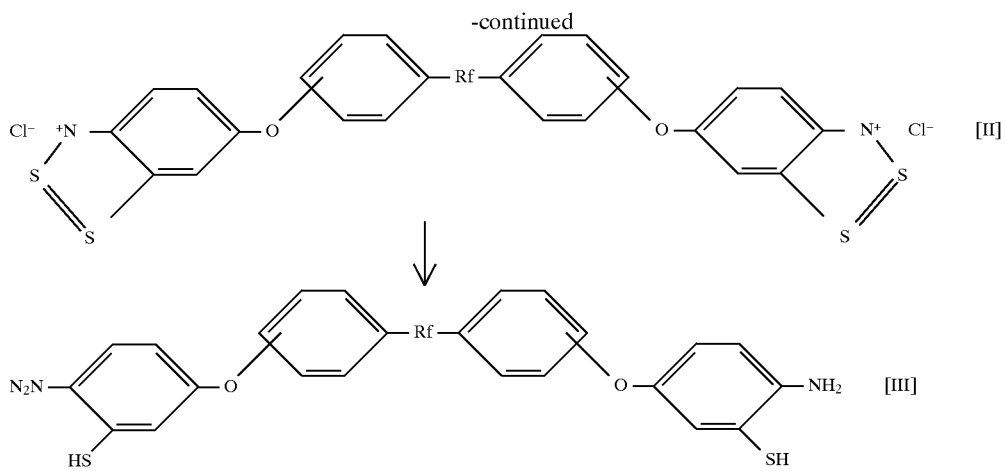

Reaction of the bisamino compound [I] with disulfur dichloride $S_2Cl_2$ (Herz reaction) is carried out at a temperature of about 50° to about 100° C. by dropwise adding $S_2Cl_2$ to a solution of the bisamino compound in glacial acetic acid, thereby forming the corresponding dithiazolium salt [II]. The dithiazolium salt is added in an inert gas atmosphere into an aqueous alkali metal hydroxide solution, and then added hydrochloric acid or the like thereto to tentatively separate a hydrochloride salt of bisaminothiophenol compound [III] or the like. Then, the hydrochloride salt or the like is dissolved in methanol, followed by addition of aqua ammonia thereto. The resulting precipitates are extracted into dichloromethane or the like, and the extract is purified through a silica gel column, whereby the desired bisaminothiophenol compound [III] can be obtained.

The desired bisaminothiophenol compound [III] can be also obtained in the following manner: Bisamino compound [I] is subjected to reaction with $NH_4SCN$ and HCl to convert $-NH_2$ groups to $-NHCSNH_2$ groups. Then, through reaction with bromine, the following bisthiazole compound [IV] is obtained:

5% by mole on the basis of the copolymer) of a perfluoro unsaturated nitrile compound.

The perfluoro unsaturated nitrile compound includes the following ones:

| | |
|---|---|
| $CF_2=CFO(CF_2)nOCF(CF_3)CN$ | (n: 2–5) |
| $CF_2=CF[OCF_2CF(CF_3)]nO(CF_2)mCN$ | (n: 1–2, m: 1–4) |
| $CF_2=CF[OCF_2CF(CF_3)]nCN$ | (n: 1–5) |
| $CF_2=CFO(CF_2)nCN$ | (n: 1–10) |

About 0.1 to about 5 parts by weight, preferably about 1 to about 3 parts by weight, of the present bisaminothiophenol compound is added as a cross-linking agent to 100 parts by weight of a fluorine-containing elastomer having CN groups as cross-linkable groups, into which the perfluoro unsaturated nitrile compound has been copolymerized. The fluorine-containing elastomer can further contain additives such as a filler, a reinforcing agent, a stabilizer, a plastilizer, a lubricant, a processing aid, etc., besides the bisaminothiophenol compound. The resulting mixture is kneaded through a roll mill or the like and then subjected to primary

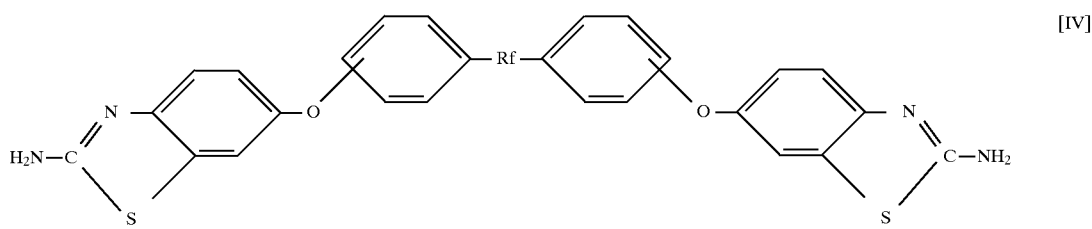

Then, the bisthiazole compound [IV] is added to an aqueous alkali metal hydroxide solution in an inert gas atmosphere, followed by addition of hydrochloric acid or the like thereto to tentatively form and separate a hydrochloride salt of bisamino-thiophenol compound [III], or the like. Then, the separated hydrochloride salt or the like is treated in the same manner as described earlier to obtain pure bisamino-thiophenol compound [III].

The thus obtained bisaminothiophenol compound can be used as a cross-linking agent for fluorine-containing elastomers having CN groups as cross-linkable groups. The fluorine-containing elastomers include copolymer elastomers each comprising tetra-fluoroethylene, perfluoro (lower alkyl vinyl ether) or perfluoro(lower alkoxy-lower alkyl vinyl ether and a small amount, e.g. about 0.1 to about vulcanization (press vulcanization) at about 160° to about 250° C. for about 30 to about 60 minutes and to secondary vulcanization (oven vulcanization), preferably in an inert gas atmosphere, at about 200° to about 300° C. for about 10 to about 50 hours.

The present invention provides a novel bisaminothiophenol compound, which can be effectively used as a cross-linking agent for fluorine-containing elastomers having CN groups as cross-linkable groups.

PREFERRED EMBODIMENTS OF THE INVENTION

The present invention will be explained in detail below, referring to Examples.

Example 1

(1) 25 ml of $S_2Cl_2$ was dropwise added to a solution containing 11.4 g (23 mM) of a bisamino compound of the following formula in 25ml of glacial acetic acid:

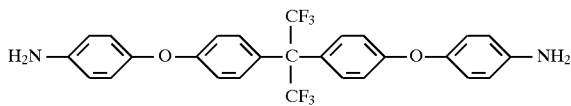

After the dropwise addition, reaction is carried out at 75° C. for 4 hours and then at 85° C. for 2.5 hours. After the reaction, the reaction mixture was cooled to room temperature, and 50 ml of dry benzene was added thereto, followed by filtration. The thus obtained residue was washed three times with dry benzene and twice with n-hexane. The washed residue was dried under reduced pressure, whereby 15.1 g of a diazolium compound of the following formula was obtained as a red solid (yield: 93%):

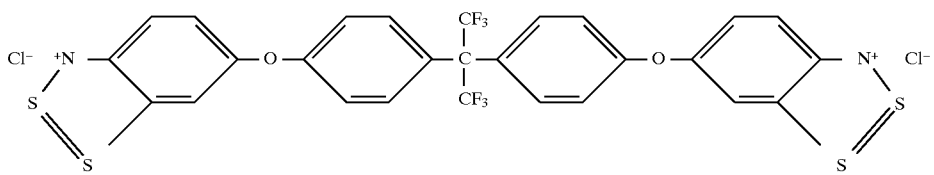

Melting point: 188°–190° C. (decomposed)
Elemental analysis ($C_{27}H_{12}F_6Cl_2N_2S_2O_2$):
Calculated; C 45.57%, H 1.98%, N 3.94%, S 18.02%
Found ; C 45.07%, H 2.09%, N 3.47%, S 18.12%
Ultraviolet absorption spectrum ($CF_3COOH$):
$\lambda$max; 370 nm($\epsilon$=16200), 445 nm($\epsilon$=18600)
$^{19}$F-NMR ($\delta$: $SO_2Cl_2$): -15.2(s)
$^{1}$H-NMR ($\delta$: $SO_2Cl_2$): 8.26(d,4H), 8.10(d,4H), 8.55(d, 2H), 9.24(d,2H), 9.72(brs,1H)

(2) 13.7 g (19.5 mM) of the thus obtained dithiazolium compound was added to 50 ml of an aqueous solution containing 9.0 g (160 mM) of potassium hydroxide in an argon gas atmosphere and subjected to reaction. The reaction mixture was extracted with dichloromethane, followed by successive addition of acetic acid and hydrochloric acid thereto. The resulting precipitates were recovered by filtration and dried, whereby 5.5 g of bisaminothiophenol . hydrochloride salt of the following formula was obtained (yield: 43%):

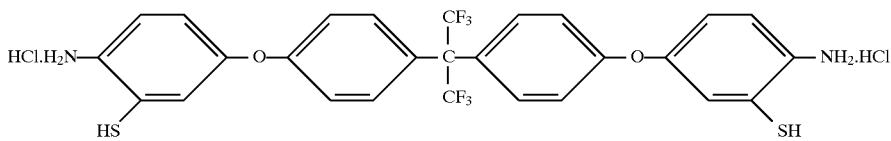

Melting point: 260°–270° C. (decomposed)
Infrared absorption spectrum ($cm^{-1}$; KBr):
2870(N—H), 2590(S—H), 1614(N—H), 1593,1489 (C=C), 1160–1265(C—F).
$^{19}$F-NMR ($\delta$: DMF-$d_6$): -13.93(s)
$^{1}$H-NMR ($\delta$: DMF-$d_6$): 7.32(d,4H), 6.73(d,4H), 6.69(d, 2H), 7.04 (d, 2H), 6.81 (brs, 1H), 6.39(brs,6H,$NH_2$+SH)

(3) 2 ml of 25% aqua ammonia was added to a solution containing 0.5 g of the thus obtained bisaminothiophenol hydrochloride salt in 10 ml of methanol. The resulting precipitates were extracted with dichloromethane, and the extract was dried over magnesium sulfate and filtered. The filtrate was subjected to distillation under reduced pressure, and the resulting residue was purified through a silica gel column (eluting solution: mixture of ethyl acetate and n-hexane in equal volumes), whereby 0.3 g of bisaminothiophenol of the following formula was obtained as a yellow solid (yield: 65%):

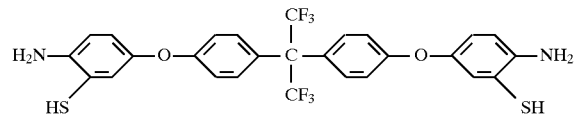

Melting point: 170° C. (decomposed)
Elemental analysis ($C_{27}H_{20}F_6N_2S_2O_2$):
Calculated; C 55.65%, H 3.44%, N 4.80%, S 11.01%
Found ; C 55.66%, H 3.58%, N 4.18%, S 10.96%
Mass spectrum: 582(M), 580(M—$H_2$), 548(M—$H_2S$)
Infrared absorption spectrum ($cm^{-1}$; in fluorohydrocarbon oil):
3470,3366($NH_2$)
3050,3029,2955,2924,2869,2857(C—H)
1613,1513,1594(C=C)
1190–1300 (C—F)
$^{19}$F-NMR ($\delta$: $C_6D_6$): -13.91(s)
$^{1}$H-NMR ($\delta$: $C_6D_6$): 3.28(brs,2H,SH), 7.51(d,4H), 6.72 (d,4H), 6.77(dd,2H), 6.16(d,2H), 6.89(d,1 H)

Example 2

200 ml of distilled water, 3.3 g of ammonium perfluorooctanoate and 2.3 g of $KH_2PO_4$ were charged into a stainless steel autoclave having a capacity of 500 ml, and then the autoclave inside gas was replaced with a nitrogen gas. Then, the autoclave was subjected to pressure reduction and cooled to 0° C.

Then, 6 g of perfluoro(5-cyanopentylvinyl ether) [CNVE], 60 g of perfluoro(methyl vinyl ether) [FMVE] and 36 g of tetrafluoroethylene [TFE] were successively charged thereto. The autoclave was heated to 60° C., and then 10 ml of an aqueous solution containing 0.15 g of sodium sulfite and 10 ml of an aqueous solution containing 1.10 g of ammonium persulfate were charged into the autoclave to initiate polymerization reaction of 16 hours' duration.

After the reaction, the ureacted gas was purged from the autoclave and the resulting aqueous latex was taken out therefrom. The aqueous latex was kept in a refrigerator at −30° C. for 24 hours for freezing. After defreezing, the coagulated polymer was washed with 10% ethanol at 50° C. and dried at 80° C. under reduced pressure for 6 hours, whereby 75 g of white terpolymer was obtained (yield: 74%). Ultraviolet absorption analysis of the terpolymer revealed absorption of CN groups at 2266cm$^{-1}$ and a copolymer composition of 1.0 mol % CNVE, 57 mol % FMVE and 42 mol % TFE.

100 parts by weight of the thus obtained terpolymer, 1 part by weight of bisaminothiophenol obtained in Example 1, 0.5 parts by weight of dicyclohexyl-18-Crown-6, 2 parts by weight of litharge and 10 parts by weight of MT carbon black were kneaded through a double roll rubber mill and then subjected to primary vulcanization at 160° C. for 30 minutes and then to secondary vulcanization at 230° C. in a nitrogen gas atmosphere for 22 hours. Normal state physical properties of the thus obtained vulcanization product were determined according to the JIS K-6301 procedure. The following results were obtained:

| Hardness (JIS-A) | 73 |
| 100% modulus | 75 kg/cm$^2$ |
| Tensile strength | 160 kg/cm$^2$ |
| Elongation | 155% |

It was found that the present bisaminothiophenol was useful as a cross-linking agent for fluorine-containing elastomers having CN groups as cross-linkable groups.

Example 3

Inside gas of a stainless steel autoclave having a capacity of 1 liter was replaced with an argon gas, and then 440 ml of distilled water, 1.1 g of ammonium persulfate, 4.6 g of KH$_2$ PO$_4$, 4.4 g of a mixture of ammonium perfluorooctanoate-ammonium perfluorodecanoate (in a ratio of 60:40 by weight) and 0.3 g of sodium sulfite were charged into the autoclave.

Then, a monomer mixture consisting of 17.8 parts by weight of perfluoro(2-methyl-3,7-dioxa-8-nonenonitrile) [FCV-82], 136.7 parts by weight of perfluoro(methyl vinyl ether) [FMVE] and 63.5 parts by weight of tetrafluoroethylene [TFE] in a molar ratio of 3:54:43 was charged into the autoclave until the autoclave inside pressure reached 6–8 kg/cm$^2$ gage. Then, the autoclave was heated to 60° C., and monomer mixture was further charged into the autoclave until the autoclave inside pressure reached 11 kg/cm$^2$ gage.

To keep the polymerization pressure at 10–11 kg/cm$^2$ gage, the monomer mixture was supplementarily supplied to the autoclave, while maintaining the polymerization temperature at 60° C. Then the polymerization reaction was continued at that polymerization temperature for further 23 hours. The autoclave inside pressure was lowered from 11 kg/cm$^2$ gage to 3–2 kg/cm$^2$ gage, and at this moment the unreacted monomer mixture was purged from the autoclave and the reaction mixture was freezed and coagulated to precipitate the polymers. The precipitated polymers were washed with hot water and then with ethanol, and dried at 60° C. under reduced pressure, whereby 169.8 g of white terpolymer was obtained. The terpolymer had a copolymer composition of 2.8 mol % FCV-82, 43.7 mol % FMVE and 53.5 mol % TFE and an intrinsic viscosity ηsp/c=0.80.

Then, 3.5 parts by weight of bisaminothiophenol obtained in Example 1 and 4 parts by weight of calcium hydroxide were added to 100 parts by weight of the thus obtained terpolymer, and the resulting mixture was kneaded through a roll mill, and subjected to primary vulcanization at 180° C. for 30 minutes and then to secondary vulcanization at 250° C. for 24 hours, Normal state physical properties of the vulcanization product were determined. The following results were obtained:

| Hardness (JIS-A) | 71 |
| 100% modulus | 50 kg/cm$^2$ |
| Tensile strength | 135 kg/cm$^2$ |
| Elongation | 200% |

It was found that the present bisaminothiophenol was useful as a cross-linking agent for fluorine-containing elastomers having CN groups as cross-linkable groups.

What is claimed is:

1. A bisaminothiophenol compound represented by the following general formula:

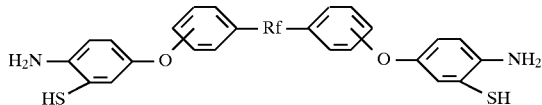

where Rf is a perfluoroalkylidene group having 1 to 10 carbon atoms, or its salt.

2. A bisaminothiophenol compound represented by the following formula:

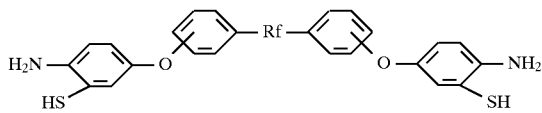

or its salt, where Rf is a perfluoroalkylidene group having 1 to 10 carbon atoms.

3. A process for producing an inorganic acid salt of a bisaminothiophenol compound represented by the following general formula [III]:

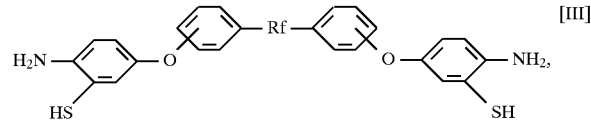

where Rf is a perfluoroalkylidene group having 1 to 10 carbon atoms, which comprises allowing a bisamino compound represented by the following general formula [I]:

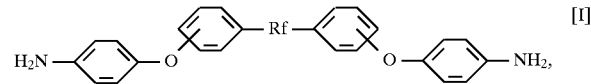

where Rf has the same meaning as defined above, to react with S$_2$Cl$_2$, thereby forming the corresponding dithiazolium salt represented by the following general formula [II]:

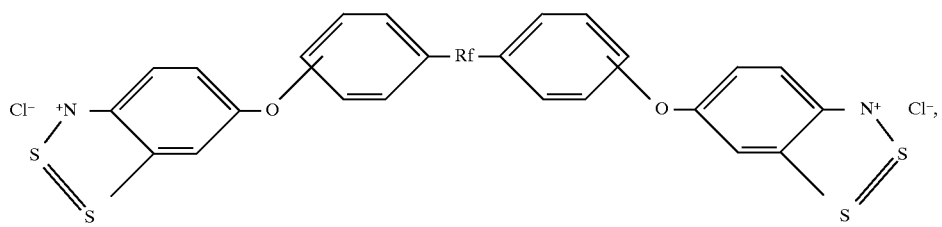

where Rf has the same meaning as defined above, and adding thereto successively an aqueous alkali metal hydroxide solution and an inorganic acid.

4. A process for producing an inorganic acid salt of a bisaminothiophenol compound represented by the following general formula [III]:

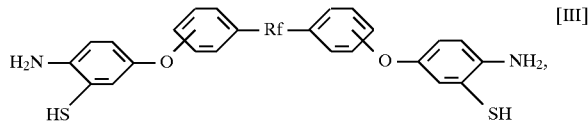

where Rf is a perfluoroalkylidene group having 1 to 10 carbon atoms, which comprises allowing a bisamino compound represented by the following general formula [I]:

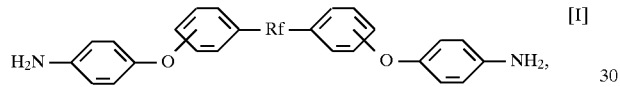

where Rf has the same meaning as defined above, to react with NH$_4$SCN and HCl, thereby forming a bisthiazole compound represented by the following general formula [IV]:

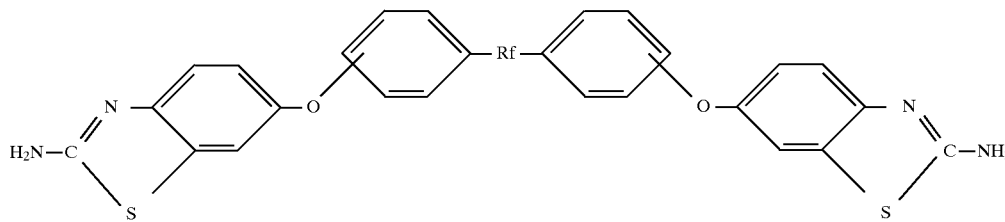

where Rf has the same meaning as defined above, and adding thereto successively an aqueous alkali metal hydroxide solution and an inorganic acid.

5. A process for producing a bisaminothiophenol compound represented by the following general formula [III]:

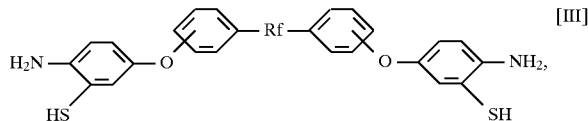

where Rf is a perfluoroalkylidene group having 1 to 10 carbon atoms, which comprises allowing an inorganic acid salt of a bisamino-thiophenol compound represented by the foregoing general formula [III] to react with aqua ammonia.

6. A cross-linking agent for fluorine-containing elastomers comprising tetrafluoroethylene, perfluoro(lower alkyl vinyl ether) or perfluoro(lower alkoxy lower alkyl vinyl ether) and perfluoro unsaturated nitrile compound having CN groups as cross-linkable groups, which comprise a bisaminothiophenol compound represented by the following general formula:

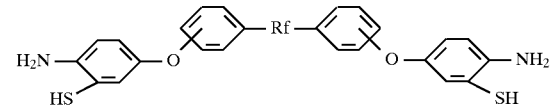

where Rf is a perfluoroalkylidene group having 1 to 10 carbon atoms.

* * * * *